United States Patent
Halevie-Goldman

(10) Patent No.: US 8,642,581 B1
(45) Date of Patent: *Feb. 4, 2014

(54) COMPOSITIONS AND METHODS FOR THE PRODUCTION OF S-ADENOSYLMETHIONINE WITHIN THE BODY

(76) Inventor: Brian D. Halevie-Goldman, Walnut Creek, CA (US)

( * ) Notice: Subject to any disclaimer, the term of this patent is extended or adjusted under 35 U.S.C. 154(b) by 1787 days.

This patent is subject to a terminal disclaimer.

(21) Appl. No.: 10/614,446

(22) Filed: Jul. 7, 2003

Related U.S. Application Data

(63) Continuation-in-part of application No. 09/781,822, filed on Feb. 12, 2001, now abandoned.

(60) Provisional application No. 60/181,799, filed on Feb. 11, 2000.

(51) Int. Cl.
*A61K 31/33* (2006.01)

(52) U.S. Cl.
USPC .......................................................... 514/183

(58) Field of Classification Search
USPC .......................................................... 514/183
See application file for complete search history.

(56) References Cited

U.S. PATENT DOCUMENTS

| | | |
|---|---|---|
| 3,962,034 A | 6/1976 | Tsuchida et al. |
| 4,242,505 A | 12/1980 | Kawahara et al. |
| 4,275,150 A | 6/1981 | Vlachakis |
| 4,369,177 A | 1/1983 | Kozaki et al. |
| 4,376,116 A | 3/1983 | Coward et al. |
| 4,558,122 A | 12/1985 | Gennari |
| 4,562,149 A | 12/1985 | Shiozaki et al. |
| 4,599,309 A | 7/1986 | Ohsumi et al. |
| 4,605,625 A | 8/1986 | Yamada et al. |
| 4,764,603 A | 8/1988 | Zappia et al. |
| 4,956,173 A | 9/1990 | Le Fur et al. |
| 4,992,282 A * | 2/1991 | Mehansho et al. ............... 426/72 |
| 5,073,546 A | 12/1991 | Zappia et al. |
| 5,087,417 A | 2/1992 | Dumbroff et al. |
| 5,100,786 A | 3/1992 | Shiomi et al. |
| 5,132,291 A | 7/1992 | Gruber |
| 5,149,701 A | 9/1992 | Shafiee et al. |
| 5,166,328 A | 11/1992 | Kurobe et al. |
| 5,198,358 A | 3/1993 | Gagliardi et al. |
| 5,264,355 A | 11/1993 | Shafiee et al. |
| 5,437,880 A * | 8/1995 | Takaichi et al. ............... 426/73 |
| 5,508,271 A * | 4/1996 | Rabinoff ............... 514/52 |
| 5,545,670 A | 8/1996 | Bissbort et al. |
| 5,569,458 A * | 10/1996 | Greenberg ............... 424/726 |
| 5,571,441 A * | 11/1996 | Andon et al. ............... 252/1 |
| 5,668,173 A | 9/1997 | Garrow |
| 5,716,941 A | 2/1998 | Rabinoff |
| 5,773,052 A * | 6/1998 | Virtanen et al. ............... 426/2 |
| 5,922,361 A | 7/1999 | Bieser et al. |
| 5,997,915 A | 12/1999 | Bailey et al. |
| 6,020,139 A | 2/2000 | Schwartz et al. |
| 6,093,703 A | 7/2000 | La Greca |
| 6,096,317 A | 8/2000 | Desantis et al. |
| 6,254,904 B1 | 7/2001 | Bailey |
| 6,555,141 B1 * | 4/2003 | Corson et al. ............... 424/725 |
| 6,914,071 B2 * | 7/2005 | Zicker et al. ............... 514/440 |
| 2001/0031744 A1 * | 10/2001 | Kosbab ............... 514/54 |
| 2002/0025926 A1 | 2/2002 | Hebert |
| 2002/0142025 A1 * | 10/2002 | Hageman ............... 424/439 |

FOREIGN PATENT DOCUMENTS

WO   WO 99/61038   * 12/1999 ............. A61K 35/78

OTHER PUBLICATIONS

Bottiglieri et al (Acta Neurol. Scand. Suppl 1994; 154:19-26 (Abstract only).*
Acta Neurol Scand Suppl 1994;154:15-8 Bell KM, Potkin SG, Carreon D, Plon L) (Abstract only).*
Betain (structure) from Betain Wikepedia May 24, 2007) 2 pages.*
Chemical Name for Vitamin B11 ( from all about vitamins (as reference) printed Jun. 4, 2007 pp. 13-16) www.natuurlijkerwijs.com.*
Geoffrey Cowley and Anne Underwood, "What is S-Adenosylmethionene (SAME)?," Newsweek. ( Jul. 5, 1999).
Chevalier, "Encyclopedia of Medicinal Plants," p. 119, ( Sep. 2, 1996).
S-Adenosylmethionine (SAMe) Part 2: Fast Acting Nat. Antidepressant, LEF Magazine, Apr. 1997, p. 1-13.
Health Notes, SAMe, Aug. 2, 1999.

* cited by examiner

*Primary Examiner* — Brandon Fetterolf
*Assistant Examiner* — Christopher R Stone
(74) *Attorney, Agent, or Firm* — John C. Serio; Seyfarth Shaw LLP

(57) ABSTRACT

Described herein is a method for increasing levels of S-adenosylmethionine within the human body without administering S-adenosylmethionine directly. The method of the invention may be achieved by administering one or more of L-methionine, methylcobalamin, 5-Methyl tetrahydrofolate, betaine, and malic acid, together with at least one compound selected from the group consisting of folic acid, vitamin $B_{12}$, magnesium, calcium, and other cofactors.

4 Claims, 1 Drawing Sheet

Figure 1         Figure 2
 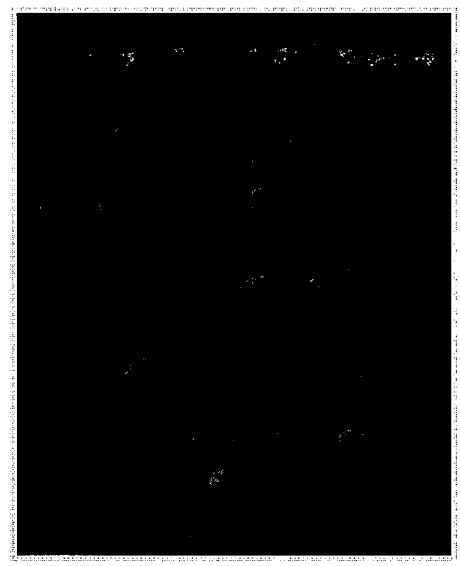

COMPOSITIONS AND METHODS FOR THE PRODUCTION OF S-ADENOSYLMETHIONINE WITHIN THE BODY

This application is a continuation in part of U.S. patent application Ser. No. 09/781,822, filed Feb. 12, 2001 now abandoned, which in turn claims the benefit of priority under 35 U.S.C. §119 of provisional application Ser. No. 60/181,799, filed Feb. 11, 2000, the contents of each of which are hereby incorporated by reference.

FIELD OF THE INVENTION

Embodiments of the present invention are directed to promoting the healthful effects of S-adenosylmethionine ("SAMe," pronounced "sammy") within the human body or other mammalian host without directly administering SAMe. The formulas disclosed herein may be used to treat conditions contrary to good mental health, to treat diseases of the liver, joints and other organs, and to promote and maintain the health of the body.

BACKGROUND OF THE INVENTION

SAMe is an important naturally-occurring substance in mammals. It plays an essential role in regulating the cell and the various biochemical processes that occur within it, from the expression of genes to the action of hormones and neurotransmitters.

SAMe is the principal methyl donor in mammals. The process of methylation is essential to building molecules and controlling the reactions between them. Most organic molecules are built along a carbon skeleton comprised of chains, rings, or other conformations of carbon atoms. The "vertebra" of this skeleton is an atom of carbon attached to three hydrogen atoms, forming a methyl group ($CH_3$). When organic molecules are assembled, it takes a certain amount of energy to attach a methyl group to a growing carbon chain. SAMe provides this energy. It contains within its structure the capacity to catalyze the transfer of single carbon or methyl groups in the most energy efficient manner. This capacity conferred survivability to the earliest self-organizing life forms and has made SAMe an important methyl donor in virtually every living organism on Earth, from single-cell prokaryotes to higher primates and human beings.

SAMe is the sulfonium form of the condensation of the high-energy compound ATP (adenosine triphosphate) and the essential amino acid methionine. Its structure is set forth below in Formula I:

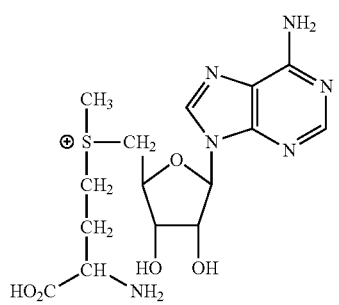

(I)

SAMe is formed within the body from methionine and ATP in a reaction catalyzed by methionine adenosyl transferase. The presence of the sulfonium ion activates the methyl group adjacent to it. This methyl group may be transferred to the amino and hydroxy acceptors of a variety of molecules, such as guanidoacetate to yield creatine, ribosomal and transfer RNA to yield methylated RNA, and norepinephrine to yield epinephrine. In addition to such transmethylation reactions, SAMe plays an important role in transsulphuration and transaminopropylation reactions, as well. For example, SAMe is a substrate of a specific lyase that converts the lyase to methylthioadenosine (MTA) and homoserine; it can be an aminoacidic chain donor in the biosynthesis of biotin; it can be a donor of the adenosyl moiety; it can be a promoter of lysin-1, 3-amino mutase, threonine synthetase, pyruvate formate lyase, and N5-methyltetrahydrofolate-homocysteine methyltransferase; it can be an inhibitor of H ribonuclease, methylene tetrahydrofolic reductase, and ethanolaminephosphate cytidyltransferase; it is important for bacterial and leukocyte chemotaxis; and it is required in the prokaryote and eukaryote restriction and modification system of DNA. U.S. Pat. No. 6,020,139 ("the '139 patent"), the disclosure of which is incorporated herein by reference, describes additional biochemical pathways by which SAMe is metabolized in the body.

On a broader level, SAMe regulates gene expression and helps prevent genetic mutations; it maintains mitochondrial function; it participates in phospholipid synthesis and maintains the integrity of cell membranes; and it regulates neurotransmitters such as serotonin, dopamine and epinephrine (Adrenaline), and hormones such as estrogen and melatonin.

Administering SAMe to subjects has been found to have a variety of salutary effects. U.S. Pat. No. 5,166,328 and U.S. Application No. 2002/0025926, the disclosures of which is incorporated by reference, describe some of these effects in the brain: it inhibits neuron death following ischemia; it improves the utilization of glucose in the brain; it inhibits brain edema; it improves EEG and evoked potential findings by normalizing them; and it improves motor function, such as that impaired by stroke. SAMe has been found, for example in meta-analyses of multiple drug studies, to enhance emotional well-being and is as effective as many common prescription drugs—tricyclics such as Elavil® (amitriptyline HCl) and Norpramin® (desipramine hydrochloride), and Selective Serotonin Reuptake Inhibitors (SSRIs) such as Prozac® (fluoxetine hydrochloride), Zoloft® (sertraline hydrochloride), and Paxil® (paroxetine hydrochloride)—in treating depression, but with significantly fewer side effects than any of these drugs. SAMe has also been used to treat anxiety, chronic pain, arthritis, rheumatoid fibromyalgia, Chronic Fatigue Syndrome, cognitive difficulties associated with Alzheimer's Disease, neurovascular disease and neurological conditions associated with AIDS. In addition to diseases of the central and peripheral nervous system, SAMe has been found to improve diseases of the joints, cardiovascular system, and liver.

Current SAMe therapy has serious shortcomings. SAMe is expensive. Preparations of SAMe cost (as of early 2001) anywhere from $1.00 to $2.50 for a single 200 mg dose. Such a dose, moreover, can benefit most subjects only mildly; treating depression, neurodegenerative disorders, and other serious conditions can require a dose of 1,600 mg or more, one to three times a day, making long-term treatment too expensive for most consumers.

SAMe is difficult to store. It is highly reactive and very hygroscopic; moisture or heat quickly degrade it. At 35° C. (95° F.), for example, SAMe will remain stable for only 8-10 hours. Making a stable SAMe salt, with tosylate, disulfate tosylate, or 1,4-butanedisulfonate, for example, increases manufacturing cost and partially accounts for the high cost of SAMe.

SAMe is difficult to administer. In most cases, SAMe is administered orally. It is sold as an over-the-counter preparation, making administration via other routes, such as by injection, suppository, or other parenteral routes, impractical or undesirable. When administered orally, some of the SAMe is consumed by intestinal flora, some of which may be pathogenic bacteria. Poor absorption of SAMe in the stomach and in the body requires the administration of large doses of SAMe to achieve the intended effect. Because SAMe is expensive, this is a serious shortcoming. As a result, much of the SAMe administered orally does not enter the bloodstream, and pharmacokinetic studies have failed to show that exogenous SAMe enters the intracellular compartment intact. SAMe contains several water-soluble groups, such as hydroxyl groups, amino groups, a sulfonium group, and a carboxyl group, and as a result has only a weak tendency to cross the lipid-rich membrane of the cell.

Administering SAMe orally can lead to serious side effects in certain individuals. SAMe can create or exacerbate an over-methylated state, leading to a manic state in individuals suffering from bipolar disorder, for example. SAMe donates a methyl group to become S-adenosyl-L-homocysteine; a hydrolase then cleaves this molecule, yielding adenosine and L-homocysteine. High levels of homocysteine have been linked to cardiovascular and neurovascular disease, and can be dangerous for individuals with high blood pressure and angina. In many susceptible individuals, administering SAMe orally may disturb the body's natural regulation of these reactions, resulting in elevated levels of homocysteine.

SUMMARY OF THE INVENTION

It is an object of the invention to achieve the beneficial effects of SAMe without the problems associated with its direct oral administration. It is a further object of the invention to provide a composition that the body can readily absorb, that is easy to manufacture, and that can increase the effectiveness of SAMe therapy. It is a further object of the invention to provide a method of achieving the beneficial effects of SAMe at less than the current high cost of SAMe therapy, thereby enabling a greater number of consumers to benefit from its effects. Still another object of the invention is to achieve the beneficial effects of SAMe without excessively elevating levels of homocysteine within the body.

Described herein is a method of increasing levels of SAMe within the body and achieving its beneficial effects without administering SAMe directly. The method of the invention comprises administering to a subject one or more of L-methionine, 5-Methyltetrahydrofolic acid, Methylcobalamin, betaine, and other cofactors.

In an embodiment of the present invention, the method comprises administering to a subject a composition comprising L-methionine, along with one or more of 5-Methyltetrahydrofolic acid (5M-THF), Methylcobalamin and betaine. In one embodiment, the composition comprises all of these compounds (L-methionine, 5-Methyltetrahydrofolic acid, Methylcobalamin and betaine). The composition may contain at least one co-factor that supports the creation of ATP in the Krebs Cycle, such as, but not limited to, a B-vitamin, alpha-lipoic acid, amino acids closely associated with the Krebs Cycle such as malic acid and L-glutamine, sulfur-containing amino acid, such as N-acetyl cysteine and taurine, minerals such as calcium, magnesium, an antioxidant and a phytonutrient. According to one method of the invention, the subject ingests during one part of the day, such as the morning, a first formulation containing L-methionine and one or more of 5M-THF, Methylcobalamin and betaine, and ingests during another part of the day, such as the evening, a second formulation comprising co-factors that are balancing, calming and leveling in contrast to the more energizing morning product. Any of the foregoing methods and compositions may be supplemented by the addition of the anxiolytic anti-convulsant mood-stabilizers kava kava and/or GABA, two compounds, which further increase the beneficial effects and improve the safety of SAMe. Since a hyper-methylated state, induced by SAMe, may in theory exacerbate a Bipolar Disorder state, and may be associated with a pro-convulsant effect in epileptic conditions, the addition of these natural anti-convulsant mood stabilizers are useful.

In order to provide all available safety measures to potential users of other products, one has to consider that the facilitation of methylation is not necessarily beneficial in two particular situations. Firstly, a state of over-methylation or a hypermethylated state may occur in the manic phase of a bipolar disorder or a florid schizoaffective psychotic state. Either those diagnosed or at risk for these conditions might be forewarned to avoid this product, or anti-convulsant mood-stabilizing ingredients may be added to diminish this risk. Substances such as kavain, dihydroxy-kavaine, methysticin, dihydro-methysticin, yangonin and desmethoxy-yangonin, and other kavalactones in the herb, Kava inhibit voltage-dependent sodium and calcium channels and have a GABA-A agonistic and an anti-glutamate action, and raise the seizure threshold and have a mood-modulatory action. Secondly, the methylation of membrane phospholipids, where only low-quality and rigid saturated fatty acids are available for methylation and are so incorporated in neuronal receptor membranes, rather than the more flexible, unsaturated free-fatty-acids (FFAs) may not well serve the adaptability of the receptor macro-molecular system to optimally adjust to changes in neurotransmitter flow.

It is a remarkable feature of the invention that one can obtain, with natural ingredients, therapeutic benefits equivalent to or greater than SAMe without administering SAMe directly, a discovery hitherto unknown in the art. The method of the invention is inexpensive, as the compositions required to perform it are inexpensive and widely available commercially. The method of the invention is moreover safer than administering SAMe directly, because increases intracellular SAMe to levels required to achieve therapeutic effect without increasing homocysteine levels.

FIGURES

FIG. 1 shows a SPECT images taken of a patient prior to using an embodiment of the invention and Omega-3 free fatty acids.

FIG. 2 shows a SPECT images taken of a patient after using an embodiment of the invention and Omega-3 free fatty acids.

DETAILED DESCRIPTION OF THE INVENTION

The method of the invention may be achieved by administering compositions comprising one or more of L-methionine, along with one or more of 5-Methyl-tetrahydrofolic acid (5M-THF), Methylcobalamin and betaine (also known as trimethyl glycine), and malic acid, together with at least one compound selected from the group consisting of folic acid, vitamin $B_{12}$, magnesium, calcium, and other cofactors. All of these compounds are inexpensive and readily available from a wide variety of commercial sources.

In a first embodiment of the invention, the method comprises administering to a subject a formulation comprising L-methionine together with a compound selected from the group consisting of betaine (also known as TMG or trimethylglycine), malic acid (or malate), folic acid (or folate), vitamin $B_{12}$ and other co-factors.

In a second embodiment of the invention, the method comprises administering to a subject a formulation comprising L-methionine together with a compound selected from the group consisting of betaine (also known as TMG or trimethylglycine), folic acid (or folate), vitamin $B_{12}$, malic acid (or malate) and other co-factors.

In a third embodiment of the invention, the method comprises administering to a subject a formulation comprising betaine and a compound selected from the group consisting of L-methionine, malic acid, folic acid, vitamin $B_{12}$ and other co-factors.

Dosing of betaine, malic acid, and L-glutamine are relative to the amounts of L-methionine. Thus, these compounds are provided in a ratio by weight of about 1:4 to about 2:1 betaine to L-methionine, about 1:12 to about 1:1 malic acid to L-methionine, and of about 1:6 to about 2:1 L-glutamine to L-methionine. In a preferred embodiment, the compounds are provided in a ratio by weight of about 1:3 to about 1:1 betaine to L-methionine, about 1:2 to about 1:3 malic acid to L-methionine, and of about 1:2 to about 1:3 L-glutamine to L-methionine.

The presence of low methionine levels creates a gradient that encourages the remethylation of homocysteine to methionine, assuming adequate amounts of the necessary co-factors, such as 5-Methyl-THF and Vitamin B12.

Because of the danger that the provision of good amounts of methionine would create unhealthful effects by increasing homocysteine levels, appropriate amounts of the anti-homocysteine and remethylation cofactors may be added to increase the health promoting effects.

Co-Factors

Compositions of the invention preferably contain at least one co-factor. As used herein, the term "co-factor" refers to those compounds that are important in the methylation process and the production of the high energy compound, adonosine-triphosphate (ATP), which is a precursor of SAMe. Preferred co-factors include alpha-lipoic acid, N-acetyl cysteine, calcium, magnesium, 5-methyl-tetrahydofolate, antioxidants (such as coenzyme $Q_{10}$, tocopherol, ascorbic acid, and lycopene), B Complex vitamins and phytonutrients, that is, extracts from certain plants that have adapted to survive at high elevations (e.g., above 16,000 feet), including, for example, *Eleuthrococcus senticosus* (Siberian Ginseng), *Rhododendron caucasium*, and certain of the *Rhodiola* species, such as *Rhodiola rosea*, *Rhodiola smythii* and *Rhodiola himalensis*. An extract of *Rhodiola Rosea* that is particularly rich in the phenylpropanoid, Rosavin would be most suitable for this purpose.

The B Complex vitamins include the hemapoietic vitamins, folic acid and B12 (in the form of methylcobalamin or hydroxycobalamin), and the energy-releasing vitamins B1 (thiamine) B2 (riboflavin), B3 (in the form of niacin or nicotinic acid or in the form of nicotinamide), B5 (pantothenate), B6 (pyridoxine) and biotin. Biotin is strictly speaking not an essential vitamin, and it is noteworthy that SAMe is required for the methylation reactions involved in the synthesis of biotin.

These and other co-factors are listed below in Table 1. The preferred dose is based on the preferred dose of L-methionine of about 2,500 mg per day. Any of the co-factors listed may be provided as their pharmaceutically acceptable salts (e.g., folate for folic acid):

| COFACTOR | PREFERRED DOSE | DOSE |
|---|---|---|
| Pyridoxine (Vitamin B6) | 10 mg | 02 mg-1,000 mg |
| Calcium Citrate | 120 mg | 0-500 mg |
| Folate or folic acid/day | 800 mcg | 0-1,000 mcg |
| Folate as Methyl tetahydrofolate/day | 600 mcg | 0-1,000 mcg |
| Alpha-lipoic acid | 100 mg | 0-500 mg |
| Choline Bitartrate | 500 mcg | 0-1 mg |
| Vitamin B12 as Methylcobalamin | 300 mcg | 0-500 mcg |
| Thiamine (Vitamin B1) | 1.5 mg | 0-2 mg |
| L-Serine | 50 mg | 0-300 mg |
| Manganese Picolinate | 1.5 mg | 0.0-2 mg |
| Riboflavin (Vitamin B2) | 10 mg | 0-10 mg |
| Biotin | 200 mcg | 0-400 mcg |
| Bioflavenoids (e.g. Quercetin) | 100 mg | 0-500 mg |
| Vitamin C | 60 mg | 0-600 mg |
| Chromium as GTF-chromium | 200 mcg | 0-200 mcg |
| Choline Bitartrate | 250 mg | 0-1,500 mg |
| Vitamin E Succinate (alpha tocopherol) | 800 IU | 0 IU-1,200 IU |
| Vitamin E (mixed tocopherols, e.g., gamma-tocopherol) | 800 IU | 0 IU-1,200 IU |
| L-Glutamine | 500 mg | 0-1,000 mg |
| N-acetyl-cysteine | 50 mg | 0-200 mg |
| Intrinsic Factor | 10 mg | 0-100 mg |
| Vitamin B3 as niacin or nicotinic acid | 20 mg | 0-200 mg |
| Vitamin B3 as niacinamide | 20 mg | 0-200 mg |
| CoEnzyme Q10 | 25 mg | 0-40 mg |
| L-Lysine | 100 mg | 0-500 mg |
| L-Threonine | 500 mg | 150-2000 mg |
| Selenomethionine or kelp extract | 150 mcg | 50-300 mcg |
| Zinc Methionate or Monomethionine | 15 mg | 5-20 mg |
| Omega-3 Free Fatty Acids | 4 g | 1-15 g |

All doses stated above are expressed as daily doses. Doses for the principal active active ingredients are set forth below in Table 2.

| COMPOUND | PREFERRED DOSE | DOSE |
|---|---|---|
| L-Methionine | 500 mg | 0-10,000 mg |
| Magnesium methionate or Magnesium monomethioninate | 500 mg | 0-10,000 mg |
| Magnesium aspartate | 180 mg | 0-5,000 mg |
| Magnesium malate | 500 mg | 0-10,000 mg |
| Malate or malic acid | 800 mg | 0-10,000 mg |
| betaine | 1,000 mg | 0-10,000 mg |

As with Table 1, all doses are expressed as daily doses. In one presently preferred embodiment, the principal active ingredients of table 2 and the co-factors of Table 1 are administered at a dose of approximately 3,000 mg total principal active ingredients and co-factors a day. This dose is preferably administered in two equivalent doses per day (that is, in two 1,500 mg doses).

The foregoing ingredients are those that promote the production of either (1) ATP; (2) L-methionine; (3) methyl-donors that re-methylate methyl-acceptors back into methyl donors and diminish the depletion of SAMe; (4) various essential nutritional co-factors (e.g., vitamins and minerals) that are important for methionine metabolism and formation of ATP but are often deficient in the diets of many individuals;

and (5) ingredients that are likely to reduce the chance of a build-up of the metabolic waste product homocysteine. These combined effect of these ingredients broaden the spectrum of conditions for which SAMe is ordinarily indicated.

While these elements may be provided to the subject through diet, the subject may also ingest them in pill, powder or liquid form. It is desirable that the methylation cofactors, particularly folate (vitamin B11), Vitamin B12 and trimethylglycine (TMG), are present. As TMG is converted to dimethyl glycine (DMG), it shifts the metabolic current away from homocysteine.

Administering L-methionine with TMG (betaine) allows intestinal flora and non-target organ systems to preferentially consume TMG (betaine) rather than L-methionine, thereby allowing a greater proportion of L-methionine to remain for use by target organ systems. Another formulation for use in the method of the invention comprises L-glutamine and L-methionine as the principal active ingredients.

L-glutamine is converted in the body into glutamate, a precursor of γ-aminobutyric acid (GABA). GABA is the principal inhibitory neurotransmitter in the brain; administering it inhibits central nervous system activity and therefore has a calming effect.

Another formulation for use in the method of the invention comprises ATP and L-methionine as the principal active ingredients. L-methionine in combination with ATP aids in the intracellular conversion of L-methionine into SAMe.

Formulations for use in the method of the invention may additionally contain vitamin B11 (folic acid) and vitamin B12 (cobalamin), to aid in the metabolism of homocysteine to methionine.

L-Glycine may also be added to the invention to facilitate methylation.

Calcium and magnesium aids in converting L-methionine into SAMe. They are preferably provided in a ratio of about two parts calcium to one part magnesium.

N-acetylcysteine also aids in converting L-methionine into SAMe, and additionally protects against a toxic build-up of homocysteine.

In another embodiment, compositions of the invention comprise L-methionine along with one or more of 5-Methyltetrahydrofolic acid (5M-THF), Methylcobalamin and betaine (also known as TMG or trimethyl glycine). These compounds are inexpensive at the small doses required and are available from commercial sources. This composition is formulated to provide a dose of about 100 mg-10,000 mg of L-methionine per day. In one embodiment, the total daily dose of L-methionine is about 600 mg per day, and may be divided over four doses of about 100 mg-150 mg.

This embodiment may contain at least one co-factor. As used herein, the term "co-factor" refers to those compounds that are important in the methylation process and the production of the high energy compound, adenosine-triphosphate (ATP), which is a precursor of SAMe. Example co-factors include alpha-lipoic acid, N-acetyl cysteine, calcium, magnesium, 5-methyl-tetrahydrofolate, antioxidants (such as coenzyme $Q_{10}$, tocopherol, ascorbic acid, and lycopene), B Complex vitamins and phytonutrients, that is, extracts from certain plants that have adapted to survive at high elevations (e.g., above 16,000 feet), including, for example, *Eleutherococcus senticosus* (Siberian Ginseng), *Rhododendron caucasium*, and certain of the *Rhodiola* species, such as *Rhodiola rosea, Rhodiola smythii* and *Rhodiola himalensis*. An extract of *Rhodiola Rosea* that is particularly rich in the phenylpropanoid, Rosavin, would be suitable for this purpose.

The B Complex vitamins include the hemapoietic vitamins, folic acid and B12 (in the form of methylcobalamin or hydroxycobalamin), and the energy-releasing vitamins B1 (thiamine) B2 (riboflavin), B3 (in the form of niacin or nicotinic acid or in the form of nicotinamide), B5 (pantothenate), B6 (pyridoxine) and biotin. Biotin is strictly speaking not an essential vitamin, and it is noteworthy that SAMe is required for the methylation reactions involved in the synthesis of biotin.

These and other co-factors are listed below in Table 3. The "preferred dose" is based on a dose of L-methionine of about 2,500 mg per day. Any of the co-factors listed may be provided as their pharmaceutically acceptable salts (e.g., folate for folic acid):

TABLE 3

Suitable co-factors to combine with active ingredients of the invention

| COFACTOR | PREFERRED DOSE | DOSE RANGE |
|---|---|---|
| Alpha-lipoic acid | 100 mg | 0-500 mg |
| Biotin | 200 mcg | 0-400 mcg |
| Calcium Citrate | 120 mg | 0-500 mg |
| Choline Bitartrate | 500 mcg | 0-1 mg |
| Chromium as GTF-chromium | 200 mcg | 0-200 mcg |
| CoEnzyme Q10 | 25 mg | 0-40 mg |
| Folate as 5-Methyl tetrahydrofolate | 600 mcg | 0-1,000 mcg |
| Folic acid | 800 mcg | 0-1,000 mcg |
| Intrinsic Factor | 10 mg | 0-100 mg |
| L-Lysine | 100 mg | 0-500 mg |
| L-Serine | 50 mg | 0-300 mg |
| L-Threonine | 500 mg | 150-2000 |
| Manganese Picolinate | 1.5 mg | 0.0-2 mg |
| N-acetyl-cysteine | 50 mg | 0-200 mg |
| Omega-3 free fatty acids (FFAs). | 4 g | 0-14 g |
| Selenomethionine or kelp extract | 150 mcg | 50-300 mcg |
| Vitamin B1 (Thiamine) | 1.5 mg | 0-2 mg |
| Vitamin B12 as Methylcobalamin | 300 mcg | 0-500 mcg |
| Vitamin B2 (Riboflavin) | 10 mg | 0-10 mg |
| Vitamin B3 as niacin or nicotinic acid | 20 mg | 0-200 mg |
| Vitamin B3 as niacinamide | 20 mg | 0-200 mg |
| Vitamin B6 (Pyridoxine) | 10 mg | 02 mg-1,000 mg |
| Vitamin C | 60 mg | 0-600 mg |
| Vitamin E (mixed tocopherols, e.g., gamma-tocopherol) | 800 IU | 0 IU-1,200 IU |
| Vitamin E Succinate (alpha tocopherol) | 800 IU | 0 IU-1,200 IU |
| Zinc Methionate or Monomethionine | 15 mg | 5-20 mg |

The foregoing co-factors 1) promote the production of either ATP or L-methionine; 2) act as methyl-donors that re-methylate methyl-acceptors back into methyl donors and diminish the depletion of SAMe; 3) provide various essential nutrients (e.g., vitamins and minerals) that are important for methionine metabolism and formation of ATP but are often deficient in the diets of many individuals; and 4) are likely to reduce the chance of a build-up of the metabolic waste product homocysteine. These combined effect of these ingredients broaden the spectrum of conditions for which SAMe is ordinarily indicated.

As to the preferred co-factors, 5-methyl-tetrahydofolate and methyl-cobalamin decrease the likelihood of SAMe depletion by providing alternative resources for methylation. B-vitamins and other co-enzymes promote the Krebs (Citric Acid) Cycle. Alpha-lipoic acid and N-acetyl-cysteine decrease the requirements for SAMe with respect to its transsulfuration pathway by providing other sulfur-containing substrates and co-factors. N-acetyl-cysteine is a precursor of the body's critical anti-oxidant, glutathione. SAMe is preserved for its other functions if it is not under oxidative pressure to convert to glutathione. Antioxidants decrease the need for the conversion of SAMe to the powerful anti-oxidant, glutathione, by providing alternative nutritional anti-oxidants. Of the broad range of anti-oxidants that may be included in this product, to decrease the channeling of SAMe to glutathione, the preferred ones include vitamins C, and E (predominantly alpha tocopherols, but gamma-tocopherols help preserve vitamin C), vitamin A, the Omega-3 free fatty acids (from fish oils or flax seed oil), anthrocyanidins (from grape seeds or Pygnogenol, from French Pine bark) and certain phytonutrients. There are particular phytonutrients that enhance the respiratory process of the Krebs Cycle even in the absence of adequate oxygenation; these derive from certain plants that have adapted to survive at high elevations where the partial pressure of oxygen is very low.

Calcium and magnesium, which are essential macro-nutrients, frequently inadequately represented in the diet of many individuals, especially those of mature years, have multiple roles in all metabolism, especially the Krebs cycle. These minerals are especially preferred co-factors. They are provided in a ratio of by weight of calcium to magnesium of about 1:2 to about 2:1. In an especially preferred embodiment, they are provided in a ratio of about 2 parts calcium to 1 part magnesium.

Examples of Conditions Treatable with the Invention

The methods of the present invention may be used to treat any condition for which SAMe is indicated.

Conditions Contrary to Good Mental Health

It is particularly effective in the treatment and prevention of conditions contrary to good mental health, especially depression. As used herein, "conditions contrary to good mental health" include any psychological or organic condition that impairs normal functioning. Examples of such conditions include, but are not limited to, somatoform disorders, such as conversion disorder, hypochondria, and body dysmorphic disorder; anxiety disorders, such panic disorder, phobias, obsessive compulsive disorder, and acute stress disorder; dissociative disorders, such as dissociative amnesia, multiple personality disorder, and depersonalization disorder; mood disorders, such as depression, dysthymic disorder, bipolar disorder (bipolar I and bipolar II disorders), cyclothymic disorder; personality disorders, such as paranoia, schizoid and schizotypal personalities, borderline personality, antisocial personality, narcissistic personality, histrionic personality, dependent personality, and obsessive-compulsive personality; psychosexual disorders, such as hypoactive sexual desire disorder and sexual aversion disorder; and schizophrenia and disorders related to it such as delusional disorder.

A condition need not be the kind that requires medical intervention to be considered a "condition contrary to good mental health." Depression, for example, encompasses major depressive disorder requiring aggressive treatment with anti-depressant medications; it also encompasses a mild case of gloominess or "feeling blue" in response to a common stressor, such as parting with a loved one for a weekend, receiving a poor grade on an exam, or even cloudy weather. There are many ways of understanding the nature of clinical depression. (Psychosocial, learned hopelessness model, interpersonal models, psychodynamic, brain systems models, as studied by neuro-imaging and electrophysiological techniques, and psychopharmacological, which focuses on the extremely complex activities at the synapse. There, fundamentally, problems can arise from (A) the neurotransmitters (analogous to keys) and (B) the receptors (analogous to keyholes). Neuropsychiatric problems may occur if there are too many or too few active neurotransmitters, or if the receptors are too up-regulated (too sensitized or too easily engaged) or down-regulated (too desensitized or resistant to engagement). The method of the invention may be used to treat any of the foregoing conditions.

Most conventional psychotropic medications, which include the anti-depressants, primarily are designed to impact (A) the neurotransmitters, by increasing or decreasing their levels, and secondarily modifying (B) the receptors, by up-regulating or down-regulating them. The present invention can benefit those taking anti-depressants by reducing the delay in anti-depressant response.

(A) In our research, two hypotheses were considered to explain the clinical observation that those patients who do not respond to tricyclic antidepressants also do not respond to SAMe.
(1) The first hypothesis postulated inadequate synthesis of neurotransmitters. Synthesis could be enhanced by mass action if sufficient neurotransmitter precursors would be provided. In this case the addition of one or more of the following: 5HTP or l-tryptophan, l-dopa, l-phenylalanine (LPA) or dl-phenylalanine (DLPA), tyrosine and/or acetyl-tyrosine, a more lipid soluble form of l-tyrosine, which is able to cross the blood-brain barrier (BBB) more efficiently, might extend the spectrum of those who could benefit to include former non-responders to other anti-depressants. Our preliminary clinical trials suggest that appears to be the case. We have on our caseload responders to our product that failed on conventional anti-depressants.
(2) Patients who do not respond to SAMe or tricyclic anti-depressants may be folate deficient. Folate deficiency was found to be a predictor of a non-response to fluoxetine (Prozac), and folate supplementation improves the response rate.

(B) This product is part of a trend in neuroscience to move away from the mono-amine hypothesis of neurotransmitter depletion towards the consideration of the receptor receiving station and not the chemical messenger per se. Then the focus shifts towards effects triggered by receptor binding, i.e. second messenger dysregulation in neuropsychiatric illness. An ideal embodiment of an effective antidepressant is one that acts not only on the turnover of neurotransmitters, but also on the receptors to which they bind.

This product represents a novel class of psychotropics that primarily impact (B) the receptors, by improving (1) the flexibility of their switching functions and (2) their constituent phospholipids.

(1) The flexibility of the receptor switching functions depends on its ability to achieve a state of suspended balance between opposing electrochemical configurations. The addition or subtraction of methyl groups (methylation and demethylation) and phosphate groups (phophorylation and dephosphorylation) are chief among these, but there are others (e.g., the often-reversible cross-linking of two sulphydral groups to form a disulfide bridge, as occurs in the vulcanization of rubber, also occurs in the ion channels of the brain). The on and off switches of phosphorylation and methylation are intimately linked in biochemical processes. For example the ratio of S-adonosyl-methionine to its metabolite S-adenosyl-homocysteine, normally about 1.5 (in adult rat liver), determines the degree of phosphorylation of the serine residues of the critical brain enzyme, phospholipid methyl-transferase. Imbalances between phophorylation and dephosphorylation occur in disturbances of the neuro-endocrine and the autonomic nervous system, causing among other things disturbances in blood sugar metabolism.

The most common cause of an imbalance between methylation and demethylation is a state of hypomethylation, which is a common factor to normal aging, depression, arthritis, and a state that predisposes to carcinogenesis. Our product is designed to address this hypomethylation.

(2) The best building blocks for the constituent phospholipids of receptor membranes would be a good balance of omega-3 and omega-6 free fatty acids (FFAs).

Associated with depression and anxiety, there is almost always an imbalance between the catabolic and anabolic processes in the body, roughly correlating with the sympathetic and the parasympathetic branches of the autonomic nervous system. The sympathetic nervous system governs "fight or flight", activation, preparation for emergencies, stresses or challenges, thickening of the blood and preparation of the clotting system of the blood to mitigate potential hemorrhage, catabolism and oxidation, temporary suspension of digestive, sexual, immunological and endocrine functions that are not immediately essential, while the parasympathetic nervous system governs "rest and repair", deactivation, thinning of the blood and anti-thrombotic activity, rest, restoration, rebuilding, anabolism and reduction or anti-oxidation.

Of the various ways that major depression can be classified or categorized there are very few that has predictive validity and reliability with respect to various treatments. The distinction between primary and secondary depression is invariably useful, as well the distinction between unipolar and bipolar depression. Both unipolar and bipolar depression can be further subdivided into an over-focused and an under-focused (or unfocused) subtype. Taking note of the presence or absence of melancholia, implying among other symptoms a severe lack of physical energy (also known as psychomotor retardation), also has predictive value as to whether or not a catechol-aminergic rather than an indole-aminergic pharmaceutical or nutraceutical medication would be likely effective. Bipolar Disorder, in the manic, depressed or mixed state, tends to be responsive to GABA'ergic medications, which are mood stabilizers, whereas the unipolar depressive disorders tend to respond to the mood elevators, i.e. the indole-aminergic (or serotonergic) agents, the catechol-aminergic (or adrenergic) agents or both. The over-focused subtype of depressive disorder (which we might call the obsessive-depressive subtype) tends to be highly responsive to the serotonergic medications, whereas the under-focused (or unfocused, or Attention Deficit Disorder (ADD)-like) subtype (which we might call the cognitively scattered subtype), is responsive (as is the melancholic subtype) to the catechol-aminergic or adrenergic pharmaceutical or nutraceutical medications or therapeutic agents. GABA'ergic, catechol-aminergic and indole-aminergic substances are available from natural sources, and may be incorporated into SAMe products, to create specific SAMe-based anti-depressants, designed to target the various subtypes of depression. Although SAMe is believed to increase turn-over of the catechol-amine, dopamine, and the indole-amine, Serotonin, the most powerful and efficacious action of SAMe is believed to be the increased fluidity of the post-synaptic membrane, upon which the chemical messengers, known as neurotransmitters act. Long term adaptive adjustments of the receptivity of this membrane are widely believed to be the critical neurophysiological events that promote and maintain good neuropsychiatric health.

When used to treat conditions contrary to good mental health, it may be desirable, depending on the condition, to add kava kava root or extracts thereof to the formulations of the invention. Kava kava, the common name for Piper methysticum, is known for its calming effects and is used to treat anxiety. Kava pyrones may be supplied as the cut or dry root of the plant, as a fluid extract, or in any of the other forms well known in the art.

A possible method is to use S-adenosyl-L-methionine (SAMe), a naturally occurring compound that appears to have a rapid onset of effect in the treatment of depression. In this open, multi-center study, 195 patients were given 400 mg of SAMe, administered parenterally, for 15 days. Depressive symptoms remitted after both 7 and 15 days of treatment with SAMe, and no serious adverse events were reported. SAMe can be used to jumpstart standard or conventional anti-depressant drugs or neutraceuticals, such as St. John's Wort.

An advantage that both the proprietary stabilized SAMe salts and our product has is that, unlike other anti-depressants on the market, such as the tricyclic anti-depressants and the selective Serotonin reuptake inhibitors (SSRIs), there is little in the way of appetite enhancement and sexual side effects. In fact our product can improve efforts at blood sugar stabilization and hence weight loss, and also actually enhance sexual libido.

Additionally, when used to treat conditions associated with a lack of energy, or to produce a weight reducing product, it may be desirable to add a source of methylxanthines, such as Gurana or Ephedra to the present invention. Methylxanthines, such as caffeine and theophylline, function as phosphodiesterase inhibitors. Their activity results in less cAMP being converted to AMP, so that more cAMP is available to activate protein kinase, which would then phosphorylate a substrate protein (e.g. an ion channel or an enzyme), to obtain a biological response at that receptor. These methylxanthines block the purinoceptor P1, (where Adenosine is the endogenous ligand), and thereby reducing it's inhibitory effect of locomotion, mental activation and post-synaptic hyper-polarization. The co-administration of one or more of the adaptogens, *Panax Ginseng, Siberian Ginseng (Eleutherococcus senticosis)*, and other adaptogens, such as *Schizandra chinensis, Withania somnifera (Ashwaganda* root) or *Cordiceps sinensis* adds to the energy enhancing effect of proprietary SAMe as well as the present invention.

Obesity and Blood Sugar Disturbances:

In Diabetes type I and II, the latter occurring co-morbidly with obesity, with greater and greater frequency, especially in younger people, there is over-activity of the phosphorylase enzyme systems while there is under-activity of the phosphatase enzyme systems. It is noteworthy that the methylation pathway's phosphatidylethanolamine methyl-transferase is activated by phosphorylation, and down-regulation of synaptic receptor membranes is often related to receptor phosphorylation.

When used to produce a weight reducing product, it may be desirable to add a source of methylxanthines, such as Gurana or Ephedra to the present invention. As discussed above, methylxanthines, such as caffeine and theophylline, function as phosphodiesterase inhibitors. Their activity results in less cAMP being converted to AMP, so that more cAMP is available to activate protein kinase, which would then phosphorylate a substrate protein (e.g. an ion channel or an enzyme), to obtain a biological response at that receptor. These methylxanthines block the purinoceptor P1, (where Adenosine is the endogenous ligand), and thereby reducing it's inhibitory effect of locomotion, mental activation and post-synaptic hyper-polarization. The co-administration of one or more of the adaptogens, *Panax Ginseng, Siberian Ginseng (Eleutherococcus senticosis)*, and other adaptogens, such as *Schizandra chinensis, Withania somnifera (Ashwaganda* root) or

*Cordiceps sinensis* adds to the energy enhancing effect of proprietary SAMe as well as the present invention.

Alcoholism and Liver Disorders.

The method of the invention may also be used to treat and prevent liver dysfunction. The term "liver dysfunction," as used herein, refers to any condition which impairs normal functioning of the liver. It includes, but is not limited to, conditions such as hepatomegaly, portal hypertension, portal-systemic encephalopathy, hepatic steatosis, fibrosis, cirrhosis, particularly alcohol-induced cirrhosis, hepatitis, hepatocellular necrosis, hepatic granulomas, hepatic cysts, and tumors of the liver, such as hepatocellular adenoma. The method of the invention may be used to treat liver dysfunction and conditions secondary to it, such as jaundice, disorders of bilirubin metabolism, and cholelithiasis.

Both SAMe as well as our product is potentially particularly valuable as a hepatoprotective supplement in cases of ongoing alcohol and polysubstance abuse. SAMe is hepatoprotective through various mechanisms, including methylation, sulfation and generation of the anti-oxidant, glutathione and this product in particular has homocysteine-lowering components. The excitatory amino acid, homocysteine and its metabolites act as agonists at the N-methyl-D-aspartate (NMDA) receptor. Over-stimulation of this NMDA receptor is believed to mediate the neuronal excitotoxicity, that predominates as the cause of neurotoxicity. Recent MRI studies from Germany correlate high homocysteine plasma levels with reduced brain hippocampal volume in chronic alcoholics. The effect was greater in the women in the study, who also had low folate, vitamin B6 and significantly high homocysteine compared to non-drinking controls. Baseline SAMe levels have been found to be lower in women than men in one study. Alcohol-induced hyper-homocysteinuria is believed to be part of the mechanism of brain damage in alcoholics. Whether this occurs by the induction of low glucose tolerance, or deficiency of folate or other B Complex vitamins is yet unclear.

L-taurine, in addition to stabilizing the mood, adds to the hepatoprotective actions of natural SAMe by being part of the sulfation detoxifying process, which is also one of SAMe's intrinsic actions. The present invention may also be used with any traditional and/or homeopathic remedies for liver dysfunction, including silymarin in milk thistle, soy isoflavones, lecithin, etc.

Arthritis and Other Diseases of the Joints:

The method of the invention may also be used to treat diseases of the joints. As used herein, "diseases of the joints" refers to any conditions which impair the normal functioning of the joints, including rheumatoid arthritis, polychondritis, systemic lupus erythematosus, connective tissue disease, ankylosing spondylitis, gout, fibromyalgia, and back pain. The method of the invention is not limited to treating those conditions for which medical intervention is necessary, but may also be used to treat anything from mild swelling of the joints to a sore back.

This product may be used to augment or have a synergistic action with other anti-arthritis nutraceuticals (e.g. Chondroitin Sulfate, and Glucosamine and galactosamine. SAMe is known to have anti-inflammatory and analgesic activity.

An example of a nutraceutical composition that will be efficacious in the treatment of arthritis (rheumatoid, osteoarthritis and other forms) would be the essential ingredients of this SAMe producing product, that would provide the methylation, transulfuration, and the associated anabolism of SAMe, in combination with (1) substances that enhance the anabolic rebuilding of cartilage, (2) that provide analgesia, (3) natural enzymes, and enhance SAMe's anti-inflammatory effects, (4) by natural corticosteroid hormonal action, (5) by COX (cyclo-oxygenase) I and II inhibition and (6) other immune-modulatory mechanisms.

(1) Glucosamine sulfate, which occurs naturally-in joint structures, stimulates cartilage regeneration, protects against joint destruction, and alleviates the symptoms of osteoarthritis. Glucosamine is used in the synthesis of Chondroitin sulfate. Methionine is known to be important in the maintenance of cartilage, especially proteoglycans and glycosaminoglycans. Various cartilage extracts, for example, Glycosaminoglycans polysulfate and activated acid-pepsin-digested calf tracheal cartilage, as well as other glycosaminoglycans, administered by injection yielded positive results in arthritis. Likewise other forms of hydrolyzed cartilage would also provide building material for synovial joint reconstruction.

(2) Both Glucosamine and Chondroitin sulfate are nutritional food supplements, well known for its use in arthritis. The proprietary stabilized salts of SAMe has been shown to augment and fortify the actions of these. Our field studies of our product have elicited reports of an impressive beneficial effect on arthritis pain, and we claim, and plan to show empirically, that our product, by increasing intracellular SAMe, provides relief by a similar mechanism.

Methyl Sulfonyl Methane or MSM is another nutritional supplement useful in arthritis. It is a useful addition to our product to decrease the drain on SAMe's trans-sulfuration pathway, and, for the treatment of arthritis, to decrease the chance of the body draining stores of sulfur from cartilage to use for its detoxification processes, in times of stress.

Dihydroepiandrosterone (DHEA) would convert to anabolic sex hormones, that would help the regrowth of eroded joint cartilage and synovium.

Pain Control (Analgesia):

SAMe has analgesic activity, thought to be due to its effect on the BH4-induced synthesis of serotonin (5-hydoxy-tryptamine or 5HT) and also the increase in 5HT turnover, as determined by an increase in serotonin's major metabolite, 5HIAA (or 5-hydoxy-indole-acetic acid). SAMe's prolongation of hexabarbital-induced sleeping time, is most likely due to its serotonergic action, since serotonergic mechanisms are mostly involved in this experimental model of sleep.

The enzymes such as Bromelain, papain and Pancreatin are beneficial for the treatment of rheumatoid arthritis and other autoimmune conditions.

In addition to pregnenalone, which is in the basic formulation, or an extract of licorice (Glycorhiza glabra) would provide natural anti-inflammatory substances with a modulated corticosteroid action, that would be beneficial in acute rheumatoid arthritis.

*Urtica dioica* (Stinging nettle) is useful for its COX (II) inhibiter effect in arthritis. The copper-dependent cyclo-oxygenases (COX enzymes) are divided into COX I and COX II enzymes. Some substances (e.g. aspirin) affect both, whereas some pharmaceuticals, developed for arthritis pain, (e.g. celexecob or Celebrex) are specific inhibitors of the COXII enzyme, that participate in the creation of the inflammatory eicosanoids. Some studies show varying specificities for COX I and COX II Inhibition among active chemical constituents involved in secondary metabolism of natural herbs.

Hyper-Estrogen States and Prevention of Gynecological Malignancies

For control of hyper-estrogen states, and for the prevention of gynecological malignancies, the combined use of the present invention and other ingredients known to be beneficial for hyper-estrogen states. These would include flax seed oil for aromatase inhibitor activity, Omega-3 FFAs, Calcium- D-Glutarate, alternative estrogen-modulating isoflavones and other phytoestrogens (e.g. lignans, Red Clover), Indole-3-Carbinol (, I3C), black cohosh, chasteberry, ginseng, dong quai, licorice, limonene and Resveratrol. (grape skin extract)

SAMe, Arthritis and Anti-Inflammatory Effect:

SAMe has anti-inflammatory activity, through various mechanisms, predominantly due to control of the eicosanoid system (by inhibiting the cyclo-oxygenase pathway of arachidonic acid, whereby leucotrienes are formed, and the reduction of leucocytes chemotaxis.). Eicosanoids are short-range cell-signaling derivates of unsaturated free fatty acids (FFAs), which comprise the group of prostaglandins, prostacyclins, leukotrienes and thromboxanes. SAMe enhances the anti-inflammatory prostaglandin E1 (PGE1) series at the expense of the pro-inflammatory prostaglandin E2 (PGE2) series. SAMe inhibits the cyclo-oxygenase metabolic pathway of the omega-6 FFA, arachidonic acid, where it is converted to pro-inflammatory leucotrienes, whereas the omega-3 FFAs would generally covert to the anti-inflammatory cytokines.

If there is sufficient SAMe's for transsulfuration, the abnormal sulfatation that occurs in the acute inflammatory phase of osteoarthritis and rheumatoid arthritis would likely seize, reverse itself and normalize.

There are numerous natural ingredients that could enhance SAMe's anti-inflammatory activity. One or more of the following would be useful in a SAMe-based anti-arthritic product. The bioflavenoids, Quercetin inhibits mast cell degranulation. Turmeric or Curcuma longa, contain the anti-inflammatory curcumins for the treatment of rheumatoid arthritis. Excessive fibrosis exacerbates many forms of arthritis, particularly if the plasma fibrinogen level is high. Another value of the quercetin and curcumin (extract from the herb Tumeric) herbs is that they are most effective in normalizing elevated fibrinogen. *Boswellia serrata* (known historically as Frankincense or Salai or Guggul in the Ayurvedic tradition) at doses of around 600 mg Boswellic acid twice daily. The extended list includes Sea Cucumber, Boron at 6-9 mg daily for osteoarthritis, Yucca leaf extract, Medicago sativa 5-10 g daily, Harpagophytum procumbens (Devil's claw) dry powdered root 3 g twice daily or dry solid extract 600 mg twice daily), *Zingibar officinalis* (ginger), *Bupleuri falcitum* and *Panax ginseng*. The trace element Copper at 1 mg daily, would be useful in addition to the calcium, magnesium and Manganese already constituents of this product. Omega 3 FFAs and also the Omega-6 FFAs, such as GLA and DGLA, reinforce the anti-inflammatory effects of SAMe.

Anabolism, Body-Building and Healing:

Guanidoacetic acid is methylated to creatine in the liver. There is an impressive body of evidence showing the anabolic benefits of creatine in body-building and in body healing. Since the absence of adequate methylation is the biggest barrier to the body's endogenous production of this beneficial body nutrient, our product which improves methylation, would render the exogenous supplementation of creatine unnecessary. Hence our claims that this product has value in body-building and wound-healing (in various situations, e.g. post-trauma or post-surgical).

The method of the invention may also be used to prevent tooth loss, facilitate lactation in pregnant women, to decrease menopausally-related sleep disturbances and other forms of insomnia, to improve the performance of athletic athletes, to improve memory, treat migraines, to treat neurodegenerative diseases such as multiple sclerosis (by repairing myelin), alleviate caffeine craving, promote the healing of ulcers, increase the effectiveness of cold medications (including herbal preparations such as Echinacea). The method may also be used to increase the effectiveness of prescription antidepressants.

Anti-Aging and Memory Preservation:

Memory Problems:

SAMe induces phospholipid methylation, improving membrane fluidity and micro-viscosity, and notably improving or reversing the age-related decrease in binding sites in beta-adrenergic receptors.

Chronic administration of SAMe to rats prevents the age-related decrease in beta-adrenergic binding sites and the age-related decrease of brain membrane fluidity, probably on the basis of its effect on phospholipid methylation.

Phenylethanolamine gets methylated by SAMe to Phosphatidylserine, which gets further methylated to Phosphatidylcholine, which is probably cleaved by the hydrolylases to be a source of the intercellular neurotransmitter, acetylcholine. Substances that increase methylation, such as folate, increase acetylcholine, which is needed to reverse cognitive decline and memory disturbances in conditions such as Alzheimer's Disorder.

Anti-Aging and Cancer-Prevention:

In creating a safe methylating product, an important problem to be solved is to create a product that would promote the growth of healthy tissues without also promoting the growth of neoplasms or cancerous tissue. In other words it should be anabolic but not carcinogenic.

An abnormal build up of polyamines are suspected of being part of the mechanism of accelerating cancer growth once it has occurred.

Safety factors, such as the inclusion of soy isoflavones, allow for an anti-estrogenic effect when the estrogen levels are too high, and a pro-estrogenic effect when the estrogen levels are too low.

Since a state of under-methylation or 'hypo-methylation' is associated with an increased propensity towards carcinogenesis, our product, which encourages methylation has a built-in safety mechanism.

This product creates a drain for homocysteine, and increase the ratio of S-adenosyl-methionine to A-adenosyl-homocysteine, which is a significant inhibitor of methylation. Our product shares with SAMe anti-aging activity and cancer-preventing activity, and is useful to be reinforcing, augmenting or having synergistic activity with other anti-aging and cancer-prevention products.

In addition to the above, research in pharmacogenomics are advancing slowly to where one can predict based on one's genome whether one might respond to a dopaminergic, a nor-adrenergic or a serotonergic pharmaceutical or nutraceutical. Some variability in various neuropsychiatric conditions have been found in somes alleles, including the DRD1,2,3,4 receptor genes, the gene coding for Dopamine-Beta-Hydroxylase, and Dopamine transporter, etc. Since proprietary SAMe and the present invention have dopaminergic and serotonergic activity, the present invention may benefit those who are found to have particular genomic configurations.

In addition to the active ingredients described herein, formulations according to the invention may optionally contain one or more excipients, including the following: preservatives, such as ethyl-p-hydroxybenzoate; suspending agents such as methyl cellulose, tragacanth, and sodium alginate; wetting agents such as lecithin, polyoxyethylene stearate, and polyoxyethylene sorbitan mono-oleate; granulating and disintegrating agents such as starch and alginic acid; binding agents such as starch, gelatin, and acacia; lubricating agents such as magnesium stearate, stearic acid, and talc; and flavoring and coloring agents.

Formulations of the present invention suitable for oral administration may be presented in any of the following forms: discrete units such as capsules, cachets, or tablets each containing a predetermined amount of the active ingredient; powder or granules; solutions or suspensions in an aqueous liquid or a non-aqueous liquid; or, as oil-in-water liquid emulsions or water-in-oil emulsions, and any other form suitable for oral administration.

In one alternative embodiment, the formulation is contained within a food stuff, such as a cookie, a bar of chocolate, a gum or jelly (e.g., a gummy bear), yogurt. It may similarly be contained in a nutrition bar, energy bar or a meal replacement bar. The formulation may be added to an egg mix to counteract the high content of cholesterol and saturated fats found in eggs. The formulation may also be added to coffee creamer (for use with decaffeinated coffee or tea) to relieve caffeine craving and to mitigate the effects of aluminum silicate commonly found in creamers.

In still further embodiments, the formulation may be added to an antacid preparation such as those containing sodium bicarbonate, aluminum hydroxide, or magnesium hydroxide. The formulation promotes methylation of DNA in the stomach, prevents stomach and gastrointestinal cancers, and promotes the healing of ulcers.

Formulations for rectal administration may be presented as a suppository with a suitable base comprising, for example, cocoa butter or a salicylate.

Formulations suitable for nasal administration may comprise either solid or liquid preparations. Where the carrier is a solid, it may be a coarse powder having a particle size, for example, in the range of 20 to 500 microns. This powder is administered in the manner in which snuff is taken, i.e., by rapid inhalation through the nasal passage from a container of the powder held close up to the nose. Where the carrier is a liquid, it may be administered as a nasal spray or as nasal drops.

Formulations suitable for vaginal administration may be presented as pessaries, tampons, creams, gels, pastes, foams, or spray formulations.

Formulations suitable for parenteral administration include, for example, aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented, for example, in unit-dose or multi-dose containers, sealed ampules and vials, and may be stored in freeze-dried (lyophilized) conditions requiring only the addition of the sterile liquid carrier immediately prior to use.

In one embodiment of the invention, a subject ingests during one part of the day, such as the morning, a first formulation containing L-methionine, 5-Methyltetrahydrofolic acid, Methylcobalamin and one or more of betaine, malic acid, and L-glutamine, and ingests during another part of the day, such as the evening, a second formulation containing co-factors (or mostly co-factors).

While the invention has been described in connection with specific exemplary embodiments, it will be apparent to those skilled in the art that various changes can be made in the structure, arrangement, proportions, elements, and materials used in the practice of the invention without departing from its principles.

Appendix Discussing Some of the Ingredients of the Invention

L-Methionine:

This product is designed to be a food supplement, catering to common deficiencies in Western diets. A diet that contains high proportions of meat, fish, poultry and eggs has many disadvantages, yet, on the positive side, it would contain adequate amounts of the essential amino acid, methionine. A high methionine diet without green leafy vegetables, that contain folic acid, would probably be unhealthy due to the likely build up of the metabolic waste product, homocysteine.

In many societies, diets that are relatively deficient in methionine are common. The most commonly lacking essential amino acids in plants are methionine, tryptophan and lysine. Practically all cereals are low in lysine. Corn and rice are also deficient in tryptophan and threonine. Legumes, even the highly nutritious soy beans and seed oils are low in methionine. Other legumes are short on methionine and tryptophan. Peanuts are deficient in methionine and lysine. Green vegetables and fruit have fairly low protein (and hence essential amino acid, especially methionine) content.

Folate, Preferably in its Methyl Form:

SAMe is needed for the synthesis of tetrahydrobiopterin (BH4), a component of folic acid, which is an essential co-enzyme for the synthesis of (what we might call the 'feel-good') monoamines, serotonin and dopamine. Most recurrently depressed individuals have been shown to have low levels of BH4, probably as a result of low SAMe levels, and in these individuals, the provision of BH4 results in remarkable improvement. BH4 is expensive and unstable, and has not been considered a commercially marketable proposition, since the body makes it readily given sufficient folic acid, Vitamin B12 and Vitamin C. For this purpose, folate may be need in doses up to 50 mg, or a proportion of this co-enzyme needs to be in the 5-Methyl-form. However folic acid's slow penetration into the central nervous system, across the blood-brain barrier (BBB) reduces the risk of it exacerbating a seizure disorder. However the methylated form of folate does not have this safeguard, and may cross the BBB in amounts that might harm those with a seizure disorder. For this reason, the ratio of folate to 5-methylfolate may need to be as high as 500:1, to be safe for a population that may include untreated, under-treated or undiagnosed subclinical epileptics.

There is a fairly common genetic variant or polymorphism, where there is relative inactivity of the enzyme that converts folic acid to its active methyl form. The enzyme known as 5,10 methylene tetrahydrofolate reductase, (hence MTHFR) aided by the methyl form of vitamin B12 creates 5-methyl-terahydrofolate (5-methyl-THF). The prevalence of the genetic MTHFR polymorphisms, such as the C677T and the A1298C, that affects the MTHFR enzyme has been reported to be from about 12% to as much as 40% of the population. It is this methyl form of folic acid, created with the help of this enzyme, which is responsible for the all-important remethylation of homocysteine back to methionine.

Now a critical problem arises when S-adenosyl-methionine is present in high concentrations in the body. As stated above, there is feedback mechanism whereby SAMe inhibits the MTHFR enzyme, the very same enzyme, whose activity may be compromised in so many genetically vulnerable people. Therefore to obtain the maximal benefits and safety of this product, a proportion of the folic acid provided must be in the pre-activated methyl form, to bypass this metabolic bottleneck.

Vitamin B12:

There is a danger to a product that provides the active form of folic acid or vitamin B11, that does not also ensure adequate amounts of vitamin B12. Both vitamin B11 (folate) and B12 deficiency may cause the hematological condition known as macrocytic anemia. That implies that the diminished number of circulating red blood cells (RBCs) have a larger mean cell volume (MCV) and have a larger mean concentration of hemoglobin (MCH). If a B12 deficiency is present in a mild form or a severe condition known as pernicious anemia, serious irreversible neurological complications are likely to be developing. Should the macrocytic anemia be treated with Vitamin B11 (folic acid) and not B12, the hematological problems would likely improve but the neurological complications would get worse. Therefore, in many cases, indiscriminant treatment with vitamin B11 (or folic acid) without vitamin B12 might mask the diagnostically important macrocytosis and exacerbate underlying neuropsychiatric illness. This is potentially even more of a problem when the 5-Methyl-THF form of folate is utilized, since the pteridine, methylene and other forms of folic acid (other than 5-methylfolate) are needed for other important metabolic processes. Absence available vitamin B12, the folic acid might get locked in its methyl form, and be unavailable for its other important metabolic roles.

Once the importance of folic acid, the methyl form of that co-factor and the need to ensure sufficient quantities of B12 is understood, the importance of the form of B12 that should be included in this product needs clarification.

The Methyl Form of B12:

It is desirable to include methylcobalamin, the methyl form of vitamin B12, in addition to the usual form of B12, which is cyanocobalamin. This is because the methyl form is much more easily absorbed in the gut, and has much better penetration across the blood-brain-barrier (BBB). The methyl form of vitamin B12, however is extremely expensive, yet very small quantities are needed to ensure adequate amounts reach their target sites. The complex absorption mechanisms for vitamin B12, and the problems that occur not uncommonly in vegetarians, elderly people, those taking ant-acids and those with various gastrointestinal conditions are well known to the medical profession and those conversant with the art. To provide a product for a broad base of the population, including a subset that might potentially have a multitude of co-morbid conditions, the presence of adequate amounts of B12 at critical target sites in the body has to be assured. In this case the brain is our primary area of concern.

For reasons of clinical efficacy as well as economy, the ratio of B12 in its (more economical) cyanocobalamin form to its methyl cobalamin form shall be between 5:1 and 50:1. An example of an ideal embodiment would have a ratio of 10:1. Similarly, for similar reasons, the ratio of vitamin B11, more commonly known as folate or folic acid, would have a ratio of the folate form to the 5-methyl-terahydrofolate form be between 5:1 and 50:1, preferably 10:1.

Intrinsic Factor (for B12 Absorption):

Intrinsic factor (IF) is a glycoprotein that plays an important role in the absorption of vitamin B12. Given sufficient quantities of stomach acid, it is secreted by the gastric parietal cells, and it facilitates absorption of B12 further down the gut in the terminal ileum. Addition of Intrinsic Factor might constitute additional insurance that sufficient B12 is absorbed into the circulation, so that alternative routes of administration (such as intramuscular or sublingual) would not be necessary. IF is available commercially extracted from the digestive tracts of pigs. This might be objectionable to followers of certain religious faiths (Jewish, Moslem, Adventist, etc.). A source other than porcine might be desirable, however such a source (e.g. bovine) would still constitute an animal product, and we want the population who can benefit, to include vegetarians. (For this purpose, we can encapsulate the product using a vegetable-derived capsule (such as "Vegicaps") instead of the "Gelcaps", which derives from gelatin of animal origin)

However it is known that if an organism consumes sufficient B12 in the diet, there is a so-called 'mass action' effect, whereby a certain portion of B12 will be absorbed from the gut into the circulation, despite low amounts or the absence of Intrinsic Factor. Therefore our preferred embodiment of our product excludes Intrinsic Factor, although it has been a component of earlier versions of our product.

Betaine (Anhydrous, Aka Trimethylglycine or TMG):

Administering betaine with L-methionine with allows intestinal flora and non-target organ systems to preferentially obtain methyl groups from betaine rather than from the L-methionine-SAMe methylation system, thereby allowing a greater proportion of L-methionine to remain for use by target organ systems. Betaine (which is Trimethyl-glycine) donates a methyl group to Homocysteine, remethylating it to thereby preventing homocysteine levels from becoming elevated. Therefore as betaine (TMG) is converted to dimethyl-glycine (DMG), it shifts the metabolic current away from homocysteine.

L-Glutamine:

L-Glutamine is oftentimes required to be diverted from the chemical intermediates involved in the Krebs cycle's function of producing the high-energy compound, ATP, to performing unique metabolic functions in the brain, as a precursor of neurotransmitters, and as a utilizable source of fuel for the brain. It is absorbed well and crosses the blood-brain-barrier (BBB) readily, far better than some neurotransmitters, such as GABA, for example.

L-glutamine can be converted in the body into the neuro-stimulating amino-acid neurotransmitter, l-glutamate, which is sometimes needed in good supply in certain low-energy brain states. At other times the brain is over-aroused, in which case, l-glutamine, in the presence of sufficient vitamin B6 (pyridoxine) and Magnesium, can be decarboxylated to γ-aminobutyric acid (GABA). GABA is the principal inhibitory neurotransmitter in the brain; administering it inhibits central nervous system activity and therefore has a calming effect.

Malic Acid:

Malic Acid is a Krebs cycle intermediate, which enhances ATP (adenosine triphosphate) production. Its normal production from succinic acid via fumaric acid may be blocked in certain metabolic disorders. The presence of tartaric acid interferes with the enzyme fumerase, and Vitamin B12 deficiency or its failure to be methylated (by SAMe) into its methyl-form that readily crosses the BBB, or its deoxyadenosylcobalamin form needed to convert methylmalonyl CoA to succinyl CoA, may result in an abundance of methylmalonic acid or malonic acid, which competitively inhibits succinate dehydrogenase, the enzyme that converts succinate to (malate's precursor) fumarate. Essentially, the provision of malic acid or its Magnesium salt, Magnesium malate, bypasses blocks in the Krebs cycle, that occur in certain hypomethylated states such as Fibromyalgia. Each molecule of malate converted to oxaloacetate creates a molecule of NADH from NAD+, which creates three molecules of ATP. Administering it with L-methionine provides the ATP that condenses with 1-methionine to form SAMe. Hence, Malic acid aids in the intracellular conversion of L-methionine into SAMe.

NADH:

NADH itself, once stabilized by a substance such as ascorbyl palmitate, is a useful addition to the product, to create more ATP to create more SAMe. Doses of NADH of 2.5 mg-50 mg a day have been found to be beneficial, particularly in the treatment of low energy states in elderly individuals. In a preferred embodiment a dose is between 5 mg and 10 mg daily.

Selenomethionine:

Selenomethionine is a well absorbed nutrient delivering the essential anti-oxidant Selenium to the tissues. Just as the methyl-transferases can convert methionine to S-adenosyl-methionine (SAMe), they can convert selenomethionine to adenosyl-selenomethionine, which was shown by Bremer and Natori in 1960[1], to be as efficient a methyl donor as S-adenosyl-methionine. For the purposes of increasing methylation in the body, Selenomethionine is useful, but only at small doses, since the preferred dose of elemental selenium is 200 mcg daily. Likewise the dose of adenosyl-selenomethionine (which is not included in this product) would be limited by potential selenium toxicity.

L-Taurine:

L-taurine helps mitigate the effects of a possible build up of polyamines, as a result of SAMe metabolism. Polyamines may increase the chances of an arrhythmia, and a composition directed at lowering the polyamines, spermine, spermidine and putescine, would likely have anti-arrhythmic properties. As with L-taurine, L-taurine, contributes to stabilizing the mood, and adds to the hepatoprotective actions of natural SAMe by being part of the sulfation detoxifying process and providing a substrate for tauroconjugation.

Kava and GABA:

When used to treat conditions contrary to good mental health, it may be desirable, depending on the condition, to add kava kava root or extracts thereof to the formulations of the invention. Kava kava, the common name for Piper methysticum, is known for its calming effects and is used to treat anxiety. Kava pyrones may be supplied as the cut or dry root of the plant, as a fluid extract, or in any of the other forms well known in the art. Kava, GABA and 1-taurine are anti-convulsant mood-stabilizing ingredients in this product, added to diminish the epileptogenic risk of 5-methyl-folate. Extracts and concentrates favoring varying ratios of the various kava-lactones in the herb, kavain, dihydoxy-kavain, methysticin, dihydro-methysticin, yangonin and desmethoxy-yangonin, and others, may be chosen as to whether the inhibition of voltage-dependent sodium and/or calcium channels are desirable, or where a serotonergic-1a ($5HT_{1A}$) effect is required or where a GABA-A agonistic and an anti-glutamate action is most needed of a particular product.

Kava and GABA have anti-arrhythmic as well as anti-convulsant activity, improving the safety of this product, and broadening the spectrum of the population it could benefit. Anti-convulsants are particularly important because of the high blood-brain-barrier penetrance of Methyl-Folate, which can lower the seizure threshold. In addition, Kava and GABA relieve mental and somatic anxiety respectfully.

Neurotransmitter Precursors:

Given sufficient quantities of 1-tryptophan or 5-hydroxy-tryptophan, the pre-synaptic nerve cells can manufacture 5-hydroxy-tryptamine, also known as serotonin. These nerve cells can produce tyrosine from phenylalanine and go on to produce 1-dopa (dihydoxy-phenylalanine) and then dopamine, nor-epinephrine (also known as nor-adrenalin) and epinephrine (adrenalin). The provision of phenylalanine and/or tyrosine increases the responder rate of a SAMe-based anti-depressant. The acetyl form of tyrosine, N-acetyl-tyrosine, crosses the blood-brain barrier more easily than tyrosine, and is also useful.

Given sufficient methylating power, as from SAMe, the body is capable of forming natural anti-depressants from methyl acceptors such as L-Dopa. A natural source of the dopamine precursor, 1-DOPA is the legume, mucuna pruriens.

SAMe is needed for the synthesis of tetrahydrobiopterin (BH4), a component of folic acid, which is an essential co-enzyme for the synthesis of (what we might call the 'feel-good') monoamines, serotonin and dopamine. Most recurrently depressed individuals have been shown to have low levels of BH4, probably as a result of low SAMe levels, and in these individuals, the provision of BH4 results in remarkable improvement. BH4 is expensive and unstable, and has not been considered a commercially marketable proposition, since the body makes it readily given sufficient folic acid, Vitamin B12 and Vitamin C. For this purpose, folate may be need in doses up to 50 mg, or a proportion of this co-enzyme needs to be in the 5-Methyl-form. Therefore the ratio of folate to methylfolate may need to be as high as 500:1, to be safe for a population that may include untreated, under-treated or undiagnosed subclinical epileptics.

BH4-mediated synthesis of the monoamines from amino-acid precursors depends on the availability of these precursor amino-acids. For those depressed individuals, with inadequate diet or absorption or over-utilization of these amino-acids and their product neurotransmitters, the inclusion of amino-acid precursors in an SAMe-based anti-depressant product, would create a broader spectrum of benefit to a wider population.

Omega-3 Free Fatty Acids:

The phospholipids associated with nerve cell receptors have an essential requirement of the diet for polyunsaturated free fatty acids (FFAs), particularly the Omega-3 FFAs, DHA (Docosahexaenoic acid) and EPA (Eicosapentaenoic acid), obtainable from fish oils, flax seed oil or, to a smaller degree, from black current seed oil. These Omega-3 FFAs are frequently deficient in modern western diets, and low levels have been shown to be low in a variety of neuropsychiatric conditions. An increasing number of studies have shown that the provision of supplementary Omega-3 FFAs have benefits for bipolar and unremitting unipolar depression and many other neuropsychiatric conditions. The inter-conversion of the nerve cell membrane phospholipids (e.g. the conversion of phosphatidylserine to phosphatidylethanolamine (PE) and then to phosphatidylcholine (PC)) involve a methylation process that depends on SAMe. About 1% of brain phosphatidylcholine (PC) constitutes a pool of PC, derived from PE methylation, which turns over rapidly and is used as an important source of choline for acetylcholine synthesis. The SAMe-dependent synthesis of this PC pool may be activated by neuronal firing. The fraction of total brain SAMe used for PE methylation (to PC) is very great, suggesting that changes in the rate of this process may influence the amounts of SAMe available for methylating other acceptors. Of importance is that this synthesized PC pool is highly enriched with polyunsaturated fatty acids.

The addition of Omega-3 FFAs may enhance the benefits of our methylation-enhancing product, particularly in those many individuals who have a less-than-adequate dietary intake of Omega-3 free fatty acids. Alternatively our methylation product would be useful to augment the benefits of the omega-3 FFAs on brain function. These omega-3 FFAs are good anti-oxidants, and therefore reduce the demand on SAMe to enter the pathway leading to the synthesis of the endogenous anti-oxidant, glutathione. However, supplemental omega-3s can interfere with the absorption of other fat-soluble vitamins, such as vitamin E and vitamin A, and other anti-oxidants, so that the dosing schedule should allow for that or the supplement regime be staggered to avoid absorption conflicts. Also FFAs, particularly unsaturated FFAs inhibit phophoethanolamine (PE) methylation in hepatocytes and microsomes. This further emphasizes the importance of dividing the doses (e.g. between morning and evening) of the Omega-3 supplementation and the provision of the methylation product, so that, for example, if one is given in the am, the other is given at night.

Omega-3 FFAs are more fluid, flexible, and function as local anti-oxidants, within neuronal structures, and when present in sufficient quantities, decreases the requirements for SAMe to be diverted towards the glutathione synthesis pathway for locally-active anti-oxidant production.

Phospholipases (such as Phospholipases A1 and A2) are responsible not only for degrading phospholipids but for remodeling them. In the case of pre- and post-synaptic receptor membranes, where fluidity and flexibility are desirable, the activity of these phospholipases may negatively affect the microviscosity of the membrane phospholipids, by bringing about the replacement of the unsaturated FFAs by saturated FFAs, if saturated FFAs and omega-6 FFAs, rather than the omega-3s are most of what is available in the diet, in most modern Western societies.

Therefore the provision of methylating compounds such as SAMe, to help synthesize membrane receptor phospholipids, such as phosphatidylcholine (also known as lecithin) can produce the most adaptable receptors to appropriately respond to the fluctuating neurotransmitter availability, if a good balance of building material is available in the form of adequate omega-3 FFA intake from dietary sources or nutritional supplementation. The benefits of a methylation-enhancing product is increased by the addition of omega-3 free fatty acids (FFAs).

Membranes with a high content of unsaturated FFAs (such as Omega-3s) are more fluid at a given body temperature when compared to membranes containing high concentrations of saturated FFAs. (Just as butter, which contains mostly saturated fats, is usually more solid than margarine, which contain more unsaturated fats, at a given temperature.) The conformation and activity of proteins intrinsic to the lipid membrane, such as neurotransmitter receptors and enzymes regulating signal transduction in neurons is believed to be highly sensitive to the difference (changes) in membrane fluidity. Omega-3s also modulates the $3^{rd}$ messenger intracellular signaling system, by directly reducing protein kinase C activity.

Phospholipids containing Omega-3 FFAs rather than saturated fats (in the inner leaflet of the lipid bilayer) appear to be a better insulator and able to dampen abnormal intracellular signal transduction. O-3s prevent the hydrolytic cleavage of PIP2 into IP3 and DAG (It does this by inhibiting the G-protein-mediated and phospholipase C-mediated hydrolysis of PIP2). Lithium and Valproic acid appear to inhibit aspects of signal transduction by actions on the inositol cycle.

Hydrolysis (phospholipase A2-mediated) of Omega-3-containing phospholipids release free Omega-3 FFAs. These free Omega-3 FFAs modulate Calcium ion influx through the L-type calcium channels. Omega-3 FFAs are thought to exert cardioprotective actions by regulating not only Calcium ion L-channels but also sodium and potassium channels. The L-type Calcium Channel blockers are good cardioprotective anti-arrhythmics as well as effective anti-convulsants and anti-manic therapeutic agents.

O-3 phospholipids are more resistant to hydrolysis by phopholipase C. Membranes are more stable. Not liable to the inositol cascade and positive feedback in mania. O-3s have AED and anti-kindling properties SAMe, Methylation and Serotonin:

Our approach was to develop and test hypotheses about the ways that SAMe produces its anti-depressant effects, and to try and facilitate the same pathways using natural products. SAMe has been shown to increase DA and 5HT turnover, as reflected by increases in forebrain and brainstem levels and their CSF and urinary metabolites, 5HIAA and HVA respectively, increases central 5HT levels and corresponding serotonergic effects on improving hexabarbital-induced sleeping time and hot-plate tests for analgesia in addition to its anti-depressant effects.

Inositol

The addition of inositol (at doses of between 250 mg-12 g) or phosphatidyl-inositol (at doses between 50 mg and 3,000 mg) would be useful to create a methylation-enhancing product with a predominantly serotonergic therapeutic action. A serotonergic product would be valuable in the treatment of major depressive disorder (MDD), particularly the sub-type where there are obsessive-depressive symptoms, obsessive-compulsive disorder (OCD), anorexia nervosa, bulimia nervosa, sleep disorders, pain disorders, panic disorder, post-traumatic stress disorder (PTSD), social phobia, anxiety disorders, Premenstrual Syndrome (PMS), also known as pre-menstrual dysphoric disorder (PMDD), sub-types of the autistic spectrum disorders, Chronic Fatigue Syndrome (CFS) and fibromyalgia.

Pregnenalone

One way of differentiating subtypes of metabolic disturbances in depression, for the sake of tailoring a treatment regime, is to consider the notion of adrenal over-activity (Cushing's. Disease) or under-activity (Addison's Disease).

Adrenalin (epinephrine) and Noradrenalin (norepinephrine) is produced and secreted from the adrenal medulla in response to an acute crisis, emergency or stress. Cortisone is produced and secreted from the adrenal cortex in response to more sub-acute or chronic stress. Prolonged stress, may causes the cortisone levels to lose its natural diurnal rhythm (higher in the am and lower in the late pm) and remain high, but eventually, if the stress persists, the levels get lower and lower as adrenal exhaustion occurs.

There are a number of herbs and natural products that are helpful in one subtype or the other, but not both. The pro-hormone, pregnenalone, however, is useful for both subtypes of depression. It sits metabolically on the crossroads, which can divert pathways towards cortisone synthesis in the adrenal exhaustion scenario, when needed, and where there are low levels of the anabolic or libido-enhancing sex hormones, it would respond to lack of end-product inhibition and produce dihydroepiandrosterone (DHEA) which may be converted to these sex hormones. DHEA has been shown to be useful in treating conditions where there is a lack of anabolism or libido problems in men and women, which depends on levels of the male sex hormone, testosterone. DHEA is therefore a useful addition to a natural anti-depressant, but may make some subtypes of depression worse. Pregnenalone is a more broad spectrum and versatile addition.

What is claimed is:

1. A composition for promoting the increase of SAMe (S-adenosylmethionine) within a human consisting of L-methionine, malic acid, wherein the ratio of malic acid to L-methionine is about 1:2 to about 1:3 by weight and one or more compounds selected from the group consisting of 5-Methyl tetrahydrofolate, methyl-cobalamin, and trimethylglycine, wherein the ratio of trimethylglycine, when selected, to L-methionine is about 1:4 to about 2:1 by weight said composition being substantially cysteine-free, and a pharmaceutically acceptable carrier composition.

2. A composition for promoting the increase of SAMe (S-adenosylmethionine) within a human consisting of L-methionine, malic acid, L-glutamine, wherein the ratio of malic acid to L-methionine is about 1:2 to about 1:3 by weight and wherein the ratio of L-glutamine to L-methionine is about 1:6 to about 2:1 by weight and one or more compounds selected from the group consisting of 5-Methyl tetrahydrofolate, methyl-cobalamin, and trimethylglycine, wherein the ratio of trimethylglycine, when selected, to L-methionine is about 1:4 to about 2:1 by weight, said composition being substantially cysteine free, and a pharmaceutically acceptable carrier composition.

3. The composition of claim 2, wherein the ratio of trimethylglycine, when selected, to L-methionine is about 1:3 to about 1:1 by weight.

4. The composition of claim 2, wherein the ratio of L-glutamine to L-methionine is about 1:2 to about 1:3 by weight.

* * * * *